United States Patent
Komatsu et al.

(10) Patent No.: US 11,642,504 B2
(45) Date of Patent: May 9, 2023

(54) SHEET MASK COMPRISING A BATTERY PART

(71) Applicant: Nippon Telegraph and Telephone Corporation, Tokyo (JP)

(72) Inventors: Takeshi Komatsu, Atsugi (JP); Masaya Nohara, Atsugi (JP); Masahiko Hayashi, Atsugi (JP); Yoko Ono, Atsugi (JP); Shuhei Sakamoto, Atsugi (JP); Yuya Uzumaki, Atsugi (JP); Mikayo Iwata, Atsugi (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 427 days.

(21) Appl. No.: 16/636,805

(22) PCT Filed: May 17, 2018

(86) PCT No.: PCT/JP2018/019012
§ 371 (c)(1),
(2) Date: Feb. 5, 2020

(87) PCT Pub. No.: WO2019/031017
PCT Pub. Date: Feb. 14, 2019

(65) Prior Publication Data
US 2020/0368510 A1   Nov. 26, 2020

(30) Foreign Application Priority Data

Aug. 7, 2017 (JP) ............................. JP2017-152157

(51) Int. Cl.
*A61M 35/00* (2006.01)
*A45D 44/00* (2006.01)
(Continued)

(52) U.S. Cl.
CPC ........... *A61M 35/10* (2019.05); *A45D 44/002* (2013.01); *A61M 37/00* (2013.01); *H01M 4/38* (2013.01);
(Continued)

(58) Field of Classification Search
CPC ................. A61M 35/10; A61M 37/00; A61M 2037/0007; A61M 2205/8206;
(Continued)

(56) References Cited

U.S. PATENT DOCUMENTS

2009/0309072 A1* 12/2009 Hwang ................... B82Y 30/00
423/447.2
2013/0143145 A1* 6/2013 Godden ................. H01M 8/188
429/535

(Continued)

FOREIGN PATENT DOCUMENTS

CN    106998889 A     8/2017
JP    2000331666 A  * 11/2000
(Continued)

OTHER PUBLICATIONS

EPO machine generated English translation of JP-2000-331666-A (Year: 2000).*
(Continued)

*Primary Examiner* — Christopher P Domone
*Assistant Examiner* — Kimberly Wyluda
(74) *Attorney, Agent, or Firm* — Kilpatrick Townsend & Stockton LLP

(57) ABSTRACT

The sheet mask includes multiple battery parts arranged such that electric currents flow along mimic muscles or flows of lymph. This allows an active ingredient to penetrate into in-body tissues more effectively and also allows the mimic muscles and the lymphatic vessels to be electrically stimulated. Forming the battery parts by using materials (Continued)

with low environmental load allows easy disposal of the sheet mask in everyday life.

8 Claims, 6 Drawing Sheets

(51) Int. Cl.
    *A61M 37/00*     (2006.01)
    *H01M 4/38*     (2006.01)
    *H01M 4/96*     (2006.01)
    *H01M 12/02*     (2006.01)
    *H01M 12/06*     (2006.01)
    *A61N 1/30*     (2006.01)
    *H01M 4/02*     (2006.01)
    *H01M 4/86*     (2006.01)

(52) U.S. Cl.
    CPC ............ *H01M 4/96* (2013.01); *H01M 12/02* (2013.01); *H01M 12/06* (2013.01); *A61M 2037/0007* (2013.01); *A61M 2205/8206* (2013.01); *A61N 1/30* (2013.01); *H01M 2004/027* (2013.01); *H01M 2004/8689* (2013.01); *H01M 2220/30* (2013.01)

(58) Field of Classification Search
    CPC ........ A45D 44/002; H01M 4/38; H01M 4/96; H01M 12/02; H01M 12/06; H01M 2004/027; H01M 2004/8689; H01M 2220/30; H01M 50/449; A61N 1/30
    See application file for complete search history.

(56) References Cited

U.S. PATENT DOCUMENTS

| | | | |
|---|---|---|---|
| 2016/0013471 A1* | 1/2016 | Kaseda | H01M 4/366 |
| | | | 429/223 |
| 2016/0089534 A1 | 3/2016 | Mohammadi et al. | |
| 2017/0141428 A1* | 5/2017 | Nakagawa | H01M 10/0568 |
| 2018/0332951 A1* | 11/2018 | Jang | A45D 44/002 |
| 2019/0046786 A1* | 2/2019 | Planard-Luong | A61N 1/327 |
| 2019/0245180 A1* | 8/2019 | Okugawa | H01M 50/423 |

FOREIGN PATENT DOCUMENTS

| | | |
|---|---|---|
| JP | 2011-166043 A | 8/2011 |
| JP | 2014-068847 A | 4/2014 |
| JP | 2014-200359 A | 10/2014 |
| WO | 2016/053683 A1 | 4/2016 |

OTHER PUBLICATIONS

International Preliminary Report on Patentability, PCT Patent Application No. PCT/JP2018/019012, dated Feb. 20, 2020.
International Search Report, PCT Patent Application No. PCT/JP2018/019012, dated Jul. 24, 2018.
Written Opinion, PCT Patent Application No. PCT/JP2018/019012, dated Jul. 24, 2018.

\* cited by examiner

US 11,642,504 B2

SHEET MASK COMPRISING A BATTERY PART

TECHNICAL FIELD

The present invention relates to a sheet mask including a battery.

BACKGROUND ART

A sheet mask formed of a sheet impregnated with lotion or solution containing a cosmetic ingredient has been used for skincare of the face. A commercially-available general sheet mask is a disposable product and can be easily handled in everyday life. Recently, proposals have been made in anticipation of further promotion of cosmetic effects. For example, there is proposed a technique in which protrusions are arranged on a sheet mask to make the positions of major acupuncture points in the face recognizable and obtain effects of acupressure in addition to activation of the skin achieved by penetration of serum (Patent Document 1). Moreover, there is also proposed a technique in which an attachable and detachable sheet electrode is attached to a sheet mask and signals are sent to the electrode by using a smartphone or the like as an external power source to cause microcurrents to flow to the skin, thereby promoting effective penetration (iontophoresis) of a cosmetic ingredient (Patent Document 2).

PRIOR ART DOCUMENT

Patent Document

Patent document 1: Japanese Patent Application Publication No. 2014-200359
Patent document 2: Japanese Patent Application Publication No. 2014-068847

SUMMARY OF THE INVENTION

Problem to be Solved by the Invention

The sheet mask provided with the protrusions has such a problem that how the fingers come into contact with protruding objects varies among individuals and not everyone can necessarily obtain the same effect. Moreover, the period for skincare with the sheet mask worn is generally referred to as a blissful period and is a period of relaxation. Accordingly, this sheet mask also has a problem that it is not psychologically easy to keep pressing acupuncture points when the sheet mask is worn.

In the method of attaching the electrode to the sheet mask and causing the microcurrents to flow from the external power source to the skin, the effective penetration of the cosmetic ingredient with the microcurrents can be expected. However, after wearing the sheet mask, the user needs to attach the electrode to the sheet mask and further connect the electrode to the external power source. Accordingly, this method has a problem that work required before the use of the sheet mask is cumbersome.

The present invention has been made in view of the aforementioned circumstances and an object thereof is to provide a sheet mask which can be expected to provide further effects while being used in the same method as a conventional general sheet mask.

Means for Solving the Problem

In order to solve the aforementioned problems, the sheet mask according to one aspect of the present invention is a sheet mask which is attached to a face for use and includes: a sheet mask main body; and a battery part arranged on the sheet mask main body and configured to come into contact with the face when the sheet mask is worn.

Effect of the Invention

The present invention can provide a sheet mask which can be expected to provide further effects while being used in the same method as a conventional general sheet mask.

MODE FOR CARRYING OUT THE INVENTION

Figure 1:
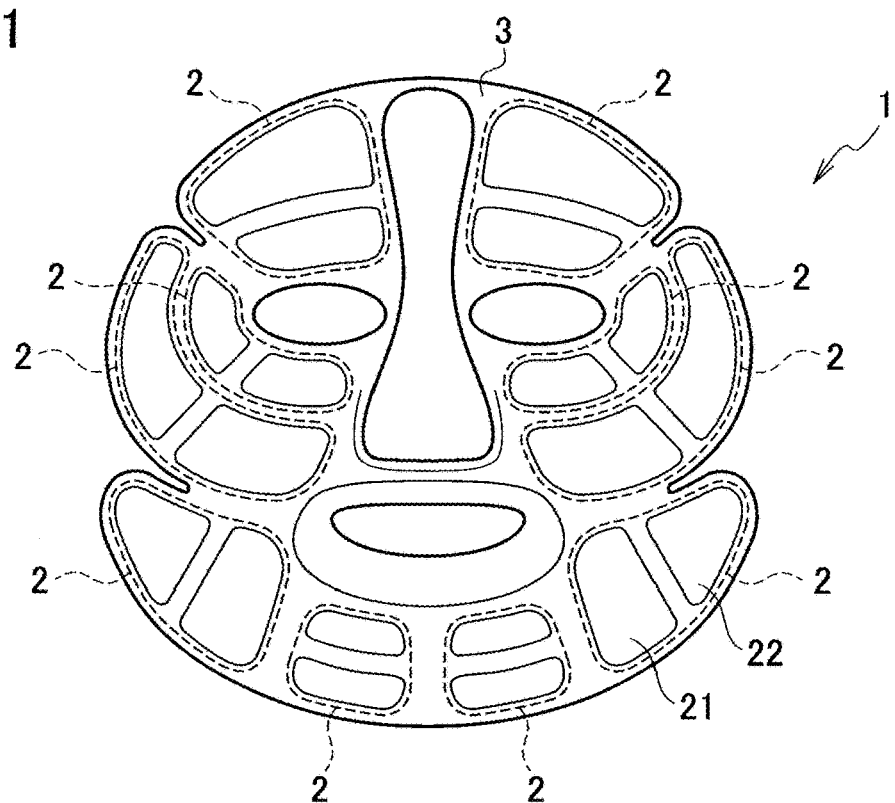
FIG. 1 is a plan view illustrating a configuration of a sheet mask in an embodiment.

An embodiment of the present invention is described below by using the drawings.
[Configuration of Sheet Mask]
FIG. 1 is a plan view illustrating a configuration of a sheet mask 1 in the embodiment. The sheet mask 1 of the embodiment includes a sheet mask main body 3 in which portions corresponding to the eyes and the mouth are cut out and multiple battery parts 2 in each of which a positive electrode portion 21 and a negative electrode portion 22 are arranged such that an electric current flows along mimic muscles. The multiple battery parts 2 are arranged over the entire surface of the sheet mask 1. When the sheet mask 1 is to be worn, the sheet mask 1 is used by impregnating the battery parts 2 with an active ingredient and bringing the positive electrode portions 21 and the negative electrode portions 22 into contact with the face.

Figure 2:
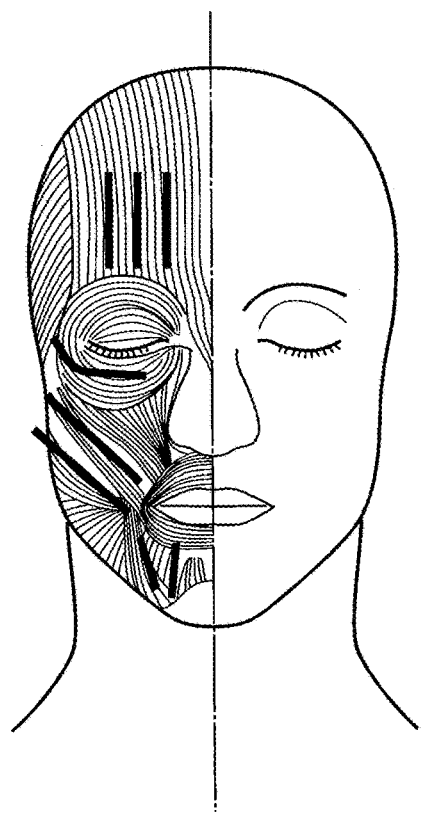
FIG. 2 is a view illustrating positions of mimic muscles.

FIG. 2 illustrates the positions of the mimic muscles. The mimic muscles are muscles which move the eyes, the mouth, the nose, and the like and weaken due to aging or the like. The weakened mimic muscles are known to lead to loss of balance in firmness of the face and the like and cause wrinkles and sagging. The sheet mask 1 of the embodiment causes lotion and solution containing the active ingredient to penetrate into a biological tissue and also electrically stimulates the muscles under the skin with microcurrents generated by battery reaction of the battery parts 2. An improvement in sagging of the muscles can be thereby expected in addition to promoting of penetration of the active ingredient. FIG. 2 illustrates the contraction directions of the mimic muscles by solid lines. The positive electrode portions 21 and the negative electrode portions 22 are arranged such that the electric currents flow along the solid lines of FIG. 2 when the sheet mask 1 of FIG. 1 is worn.

[Configuration of Sheet Mask in Modified Example]

Figure 3:
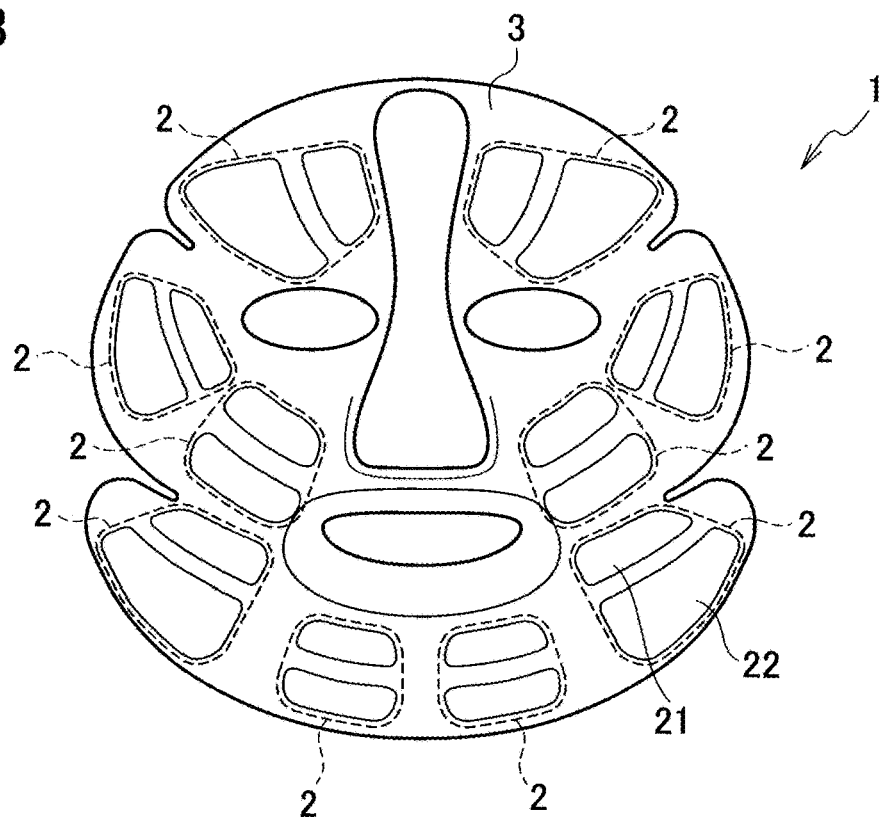
FIG. 3 a plan view illustrating a configuration of a sheet mask in a modified example.

FIG. 3 is a plan view illustrating a configuration of a sheet mask 1 in a modified example. The sheet mask 1 in the modified example includes the sheet mask main body 3 in which portions corresponding to the eyes and the mouth are cut out and the multiple battery parts 2 in each of which the positive electrode portion 21 and the negative electrode portion 22 are arranged such that an electric current flows along a flow of lymph in the face. The multiple battery parts 2 are arranged over the entire surface of the sheet mask 1. When the sheet mask 1 is to be worn, the sheet mask 1 is used by impregnating the battery parts 2 with the active ingredient and bringing the positive electrode portions 21 and the negative electrode portions 22 into contact with the face.

In the sheet mask 1 in the modified example, the configurations and functions of the battery parts 2 are the same as those in the sheet mask 1 of FIG. 1. However, the arrangement of the positive electrode portions 21 and the negative electrode portions 22 is different and the directions in which the microcurrents flow are different.

Figure 4:
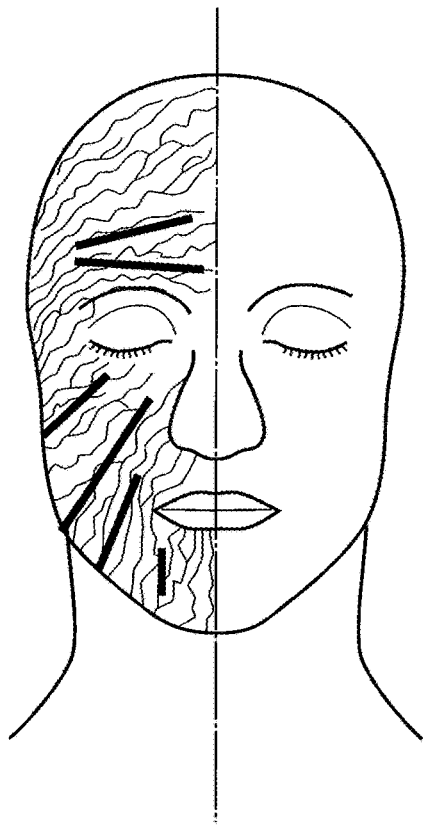
FIG. 4 is a view illustrating flows of lymph in the face.

FIG. 4 illustrates flows of lymph in the face. The lymph refers to lymph fluid flowing through lymphatic vessels extending across the entire body like blood vessels. It is known that, when the flow of lymph stagnates, excessive water in the body cannot be excreted and this leads to swelling of the body and to a decrease in immune functions due to deposit of waste products included in the water. The sheet mask 1 in the modified example causes lotion and solution containing the active ingredient to penetrate into the biological tissue and also electrically stimulates the lymphatic vessels with the microcurrents generated by the battery reaction of the battery parts 2. Promoting of excreting of waste products can be thereby expected in addition to promoting of penetration of the active ingredient. FIG. 4 illustrates the flows of lymph by solid lines. The positive electrode portions 21 and the negative electrode portions 22 are arranged such that the electric currents flow along the solid lines of FIG. 4 when the sheet mask 1 of FIG. 3 is worn.

[Configuration of Battery]

Next, each of the battery parts 2 arranged in the sheet mask 1 is described. The battery part 2 described below can be applied to both of the sheet mask 1 of FIG. 1 and the sheet mask of FIG. 3.

Figure 5:
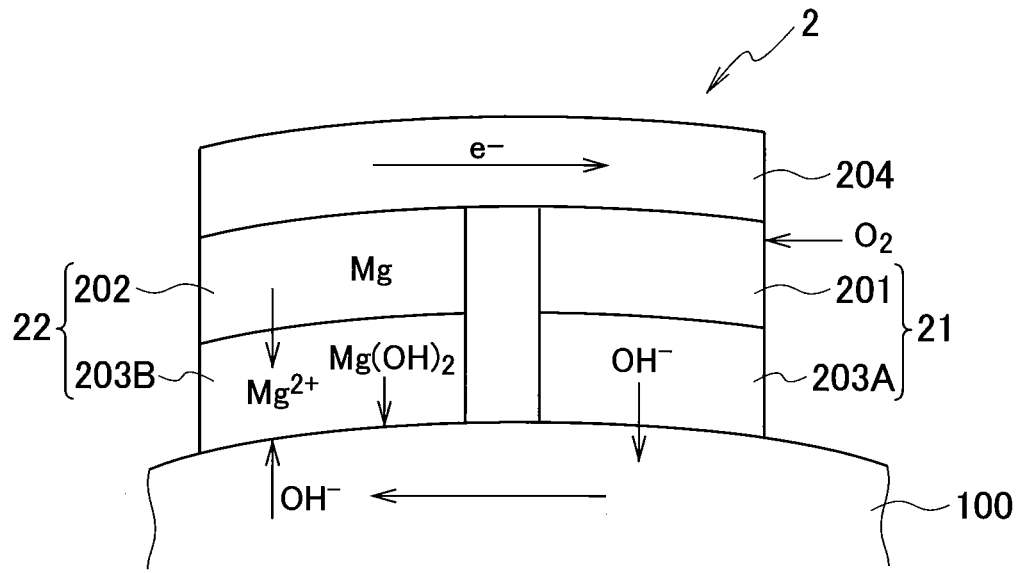
FIG. 5 is a view illustrating an outline of a cross-sectional configuration of a battery part.

FIG. 5 is a view illustrating an outline of a cross-sectional configuration of the battery part 2. FIG. 5 illustrates compounds relating to reaction together with the elements forming the battery part 2. Although a battery using magnesium is described herein, the present invention is not limited to the battery using magnesium and batteries using aluminum, zinc, and manganese, a bio-fuel cell with high biocompatibility, and the like can be also used.

The battery part 2 includes the positive electrode portion 21, the negative electrode portion 22, and an electrically-conductive layer 204 electrically connecting the positive electrode portion 21 and the negative electrode portion 22 to each other. The positive electrode portion 21 includes a positive electrode 201 and a positive electrode portion separator 203A arranged in contact with the positive electrode 201 and out of contact with a negative electrode 202. The negative electrode portion 22 includes the negative electrode 202 formed to contain magnesium and a negative electrode portion separator 203B arranged in contact with the negative electrode 202 and out of contact with the positive electrode 201. Unlike a general magnesium-air battery, in the battery part 2 of the embodiment, the positive electrode portion separator 203A and the negative electrode portion separator 203B are out of contact with each other. Moreover, the positive electrode portion separator 203A and the negative electrode portion separator 203B contain no electrolyte.

The positive electrode portion separator 203A and the negative electrode portion separator 203B are impregnated with the active ingredient and are brought into contact with a biological tissue (skin) 100. The active ingredient thereby serves the role of the electrolyte of the battery part 2 as well as the role of a cosmetic ingredient and the battery reaction starts in the battery part 2.

A positive electrode used in a general magnesium-air battery can be used as the positive electrode 201. For example, carbon, metal, oxide, nitride, carbide, sulfide, or phosphide can be used. Two or more of these materials may be mixed. The positive electrode 201 may support a catalyst. Metal, oxide, nitride, carbide, sulfide, or phosphide can be used as the catalyst. Two or more of these materials may be mixed.

The positive electrode 201 can be fabricated in publicly-known processing of shaping carbon powder with a binder. However, a resin containing fluorine is generally used as the binder and, when the positive electrode 201 is combusted in disposal or the like, hydrofluoric acid is generated. Using carbonized bacterial cellulose or cellulose nanofiber carbon for the positive electrode 201 eliminates the need for the resin containing fluorine. As a result, the sheet mask 1 of the embodiment can reduce the environmental load and be easily disposed in everyday life. The carbonized bacterial cellulose and the cellulose nanofiber carbon are both carbonized cellulose with a three-dimensional network structure.

The negative electrode 202 is made of a negative electrode active material. The negative electrode active material may be any material which can be used as a negative electrode material of a magnesium-air battery, that is any material containing metal magnesium or a magnesium-containing substance. Materials other than magnesium which can be used for a metal-air battery such as iron, zinc, aluminum, calcium, lithium, and sodium can be also used as the negative electrode material.

The positive electrode portion separator 203A and the negative electrode portion separator 203B may be made of any substance which can contain the active ingredient and has no electrical conductivity. For example, Japanese paper, cotton, collagen, bacterial gel, or bacterial xerogel can be used.

The material of the electrically-conductive layer 204 is not limited to a particular material and may be any material as long as it is electrically conductive. Examples of the material include a carbon cloth, a carbon sheet, a metal mesh, a metal wire, an electrically-conductive cloth, an electrically-conductive rubber, and an electrically-conductive polymer. The positive electrode portion 21 and the negative electrode portion 22 may be arranged on the sheet mask main body 3 with the sheet mask main body 3 serving as the electrically-conductive layer 204.

The "active ingredient" of the embodiment refers to water, alcohol, a drug solution which has an effect on a specific disease, or a cosmetic liquid which is used to clean and beautify the body of a human, make a person more attractive, change the appearance, and maintain the skin or hair healthy. The active ingredient may be any substance in which magnesium ions and hydroxide ions are movable between the positive electrode 201 and the negative electrode 202 via the biological tissue 100. Examples of the active ingredient include organic and inorganic acids, derivatives thereof, and solution containing salts of these acids.

[Electrode Reaction]

Electrode reactions in the positive electrode 201 and the negative electrode 202 are described.

Water contained in the active ingredient and oxygen in air come into contact on a surface of the positive electrode 201 and the reaction illustrated in the following formula (1) thereby progresses.

$$O_2+2H_2O+4e^-\rightarrow 4OH^- \qquad (1)$$

Meanwhile, in the negative electrode 202 in contact with the active ingredient, the reaction illustrated in the following formula (2) progresses. Specifically, magnesium forming the negative electrode 202 discharges electrons and dissolves into the active ingredient as magnesium ions.

$$Mg\rightarrow Mg^{2+}+2e^- \qquad (2)$$

These reactions occur via the biological tissue 100 and the active ingredient impregnated into the positive electrode portion separator 203A is introduced into the biological tissue 100 together with hydroxide ions ($OH^-$). In the sheet mask 1 of FIG. 1, the movement of the hydroxide ions stimulates the muscles and improvements in the sagging of the muscles can be thereby expected. In the sheet mask 1 of FIG. 3, the movement of the hydroxide ions stimulates the lymphatic vessels. This improves flow of the lymph fluid in the lymphatic vessels and promotes excretion of the waste products in the body and improvements in swelling, stiffness, and sagging can be expected.

The entire reaction of the battery reactions is as illustrated in the following formula (3) and is reaction of generating magnesium hydroxide.

$$2Mg+O_2+2H_2O+4e^-\rightarrow 2Mg(OH)_2 \qquad (3)$$

Theoretical electromotive force is about 2.7 V.

[Configuration of Battery of Modified Example]

Figure 6:
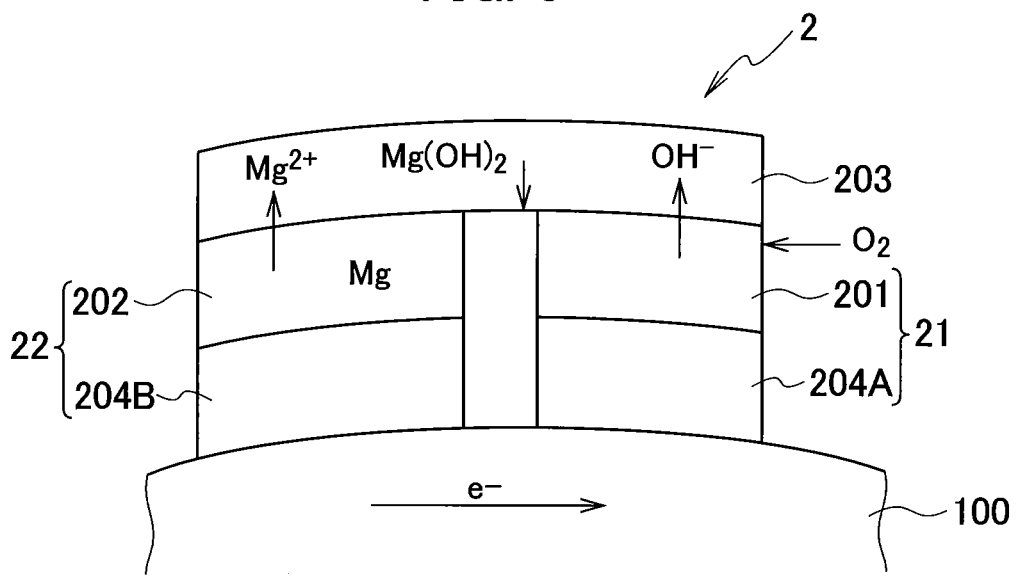
FIG. 6 is a view illustrating an outline of a cross-sectional configuration of a battery part in a modified example.

FIG. 6 is a view illustrating an outline of a cross-sectional configuration of the battery part 2 in a modified example. The battery part 2 in the modified example may be used in the sheet masks 1 of FIGS. 1 and 3.

The battery part 2 of FIG. 6 includes the positive electrode portion 21, the negative electrode portion 22, and a separator 203 arranged in contact with the positive electrode portion 21 and the negative electrode portion 22. The positive electrode portion 21 includes the positive electrode 201 and a positive electrode portion electrically-conductive layer 204A arranged in contact with the positive electrode 201 and out of contact with the negative electrode 202. The negative electrode portion 22 includes the negative electrode 202 formed to contain magnesium and a negative electrode portion electrically-conductive layer 204B arranged in contact with the negative electrode 202 and out of contact with the positive electrode 201. Unlike a general magnesium-air battery, in the battery part 2 of the embodiment, the separator 203 contains no electrolyte.

When the battery part 2 is to be attached to the biological tissue 100, the separator 203 is impregnated with the active ingredient. The active ingredient thereby serves the role of the electrolyte of the battery part 2 as well as the role of a cosmetic ingredient and the battery reaction starts in the battery part 2.

The same elements as the battery part 2 in FIG. 5 can be used as elements of the battery part 2 in the modified example. The positive electrode portion 21 and the negative electrode portion 22 may be arranged on the sheet mask main body 3 with the sheet mask main body 3 serving as the separator 203.

The battery part 2 in the modified example is different from the battery part 2 of FIG. 5 in that the positive electrode portion electrically-conductive layer 204A and the negative electrode portion electrically-conductive layer 204B are brought into contact with the biological tissue 100 and electrons ($e^-$) are made to move to the biological tissue 100.

Electrode reaction is the same as that in the battery part 2 of FIG. 5. In the battery part 2 of the modified example, anionic species and cationic species of the active ingredient penetrate into the biological tissue 100 with the flow of electrons into the biological tissue 100. The electric current flows in the biological tissue 100 and stimulates the muscles or the lymphatic vessels and improvements in the sagging of the muscle or improvements in the action of excreting waste products can be thereby expected.

[Examples and Evaluation Results]

Next, description is given of examples varying in the materials of the elements in the battery part 2 and of evaluation results of these examples.

EXAMPLE 1

Figure 7:
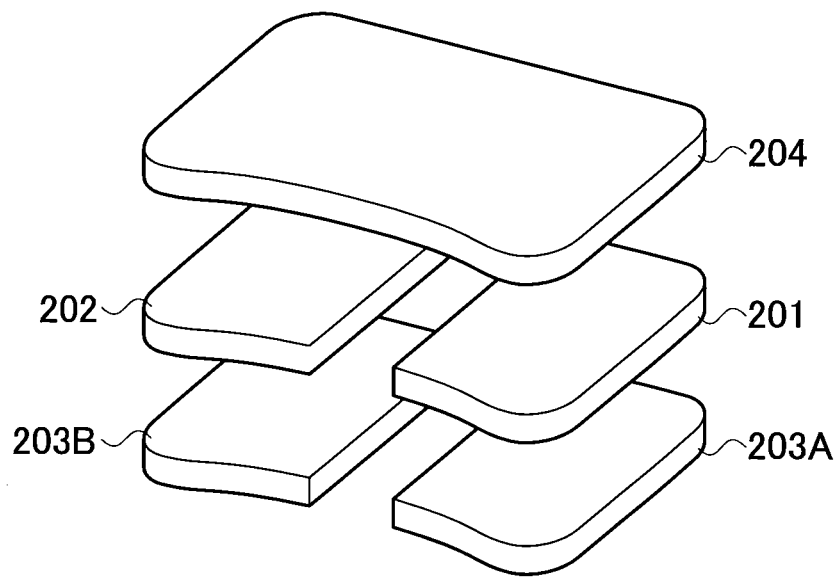
FIG. 7 is an exploded perspective view of a battery part in Example 1.
Figure 8:
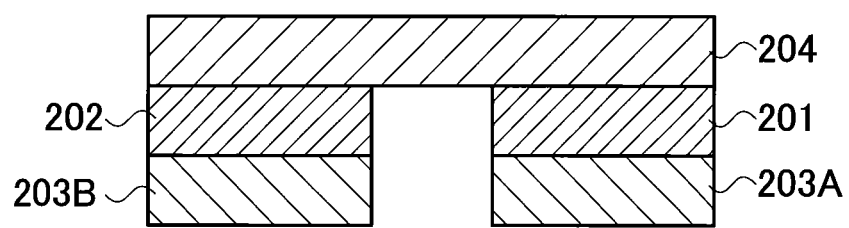
FIG. 8 is a cross-sectional view of the battery part in Example 1.

FIG. 7 is an exploded perspective view of the battery part 2 in Example 1. FIG. 8 is a cross-sectional view of the battery part 2 in Example 1.

The battery part 2 of Example 1 included the positive electrode 201, the negative electrode 202, the positive electrode portion separator 203A, the negative electrode portion separator 203B, and the electrically-conductive layer 204. In Example 1, the carbonized bacterial cellulose which was carbonized cellulose with a three-dimensional network structure was used for the positive electrode 201. Preparation of the battery part 2 of Example 1 is described below.

The carbonized bacterial cellulose used in the positive electrode 201 was obtained in the following method.

First, nata de coco (manufactured by Fujicco) which was a bacteria cellulose gel produced by acetobacter xylinum being acetobacter was used as the bacterial gel and the bacterial gel was immersed in liquid nitrogen for 30 minutes in a styrene foam box to be completely frozen. After the bacterial gel was completely frozen, the frozen bacterial gel was taken out and put on a petri dish and was dried in vacuum of 10 Pa or less by using a freeze dryer (manufactured by Tokyo Rikakikai Co, Ltd) to obtain a bacterial xerogel. After the drying in vacuum, the bacterial xerogel was carbonized by being baked at 1200° C. for two hours in a nitrogen atmosphere and the carbonized bacterial cellulose was obtained.

XRD measurement, SEM observation, porosity measurement, tensile test, and BET specific surface area measurement were performed to evaluate the obtained carbonized bacterial cellulose. It was confirmed in the XRD measurement that the carbonized bacterial cellulose was a carbon (C, PDF card No. 01-071-4630) single-phase material. The PDF card No. is a card number of PDF (Powder Diffraction File) which is a database collected by International Centre for Diffraction Data (ICDD). It was confirmed in the SEM observation that the carbonized bacterial cellulose was a bicontinuous body in which nanofibers with a diameter of 20 nm were continuously connected. The BET specific surface area of the carbonized bacterial cellulose was measured by using a BET apparatus and was 830 m$^2$/g. The porosity of the carbonized bacterial cellulose was measured by performing mercury intrusion porosimetry and was 99% or more. The porosity was calculated from a pore size distribution of the carbonized bacterial cellulose obtained by the mercury intrusion porosimetry with pores modeled as cylindrical shapes. It was confirmed from the results of the tensile test that, when strain of 80% was applied by tensile stress, the tensile stress did not exceed the elastic region and the carbonized bacterial cellulose returned to its shape before the application of the stress. Thus, it was found that the bacterial cellulose had an excellent elastic property also after being carbonized.

The positive electrode 201 was fabricated by cutting out the obtained carbonized bacterial cellulose into a desired shape by using a blanking blade, a laser cutter, and the like.

The negative electrode 202 was fabricated by cutting out a commercially-available metal magnesium foil (thickness: 200 μm. manufactured by Nilaco Corporation) into a desired shape by using a blanking blade, a laser cutter, and the like.

The positive electrode portion separator 203A and the negative electrode portion separator 203B were fabricated by cutting out a commercially-available cellulose cotton (BEMCOT, manufactured by Asahi Kasei Corporation) into a desired shape by using a blanking blade, a laser cutter, and the like.

The electrically-conductive layer 204 was fabricated by cutting out a commercially-available carbon cloth (manufactured by TORAY industries, Inc.) into a desired shape by using a blanking blade, a laser cutter, and the like.

The battery part 2 was fabricated by using the aforementioned elements as follows. First, the positive electrode 201 and the negative electrode 202 were laid on the electrically-conductive layer 204 and were sandwiched between the electrically-conductive layer 204, the positive electrode portion separator 203A and the negative electrode portion separator 203B. In this case, the positive electrode 201 and the negative electrode 202 were arranged out of contact with each other. Portions 1 mm inside outer peripheries of the positive electrode 201 and the negative electrode 202 were sewed by using a sewing machine to pressure-bond these elements to one another and the battery part 2 was thus obtained.

As illustrated in FIG. 1, the multiple battery parts 2 were arranged on the sheet mask main body 3.

The active ingredient for starting the battery reaction was prepared as follows. A carbonate aqueous solution with pH of 8.8 and an L-ascorbic acid (vitamin C) aqueous solution with concentration of 100 μmol/ml were mixed such that a mixture with pH of about 7.4 was prepared. Although the L-ascorbic acid was used as the active ingredient in Example 1, the active ingredient is not limited to this.

In the evaluation test, the sheet mask 1 of Example 1 impregnated with the active ingredient was attached to a subject and, after 15 minutes, the moisture amount in the skin was measured. The positive electrode portion separator 203A and the negative electrode portion separator 203B were sufficiently impregnated with the active ingredient to start the battery reaction. After it was checked that the positive electrode portion separator 203A and the negative electrode portion separator 203B of each battery part 2 were soaked with the active ingredient, the sheet mask 1 was attached to the face of each of 100 subjects aging from teens to sixties to perform skincare for 15 minutes and the moisture amount in the skin was measured. The moisture amount was measured by using a skin moisture checker (manufactured by Scalar Corporation).

Results of the evaluation test are described later.

EXAMPLE 2

Example 2 was different from Example 1 in that a carbonized bacterial cellulose sheet containing carbonized bacterial cellulose and bacterial cellulose was used for the positive electrode.

The carbonized bacterial cellulose sheet used for the positive electrode 201 was obtained by the following method. The carbonized bacterial cellulose fabricated in Example 1 was impregnated with water and then the carbonized bacterial cellulose and bacterial gel were mixed at a weight ratio of 1:1 and stirred in a homogenizer (manufactured by SMT CO., LTD.) for 12 hours to obtain a mixture in a slurry form. Then, the mixture was subjected to suction filtration by using an aspirator (manufactured by Sibata Scientific Technology LTD.) and the mixture was peeled off from filter paper to obtain a carbonized bacterial cellulose sheet. Thereafter, the carbonized bacterial cellulose sheet was put into a thermostat chamber and subjected to drying processing at 60 degrees Celsius for 12 hours to fabricate the carbonized bacterial cellulose sheet used for the positive electrode 201 of Example 2.

The carbonized bacterial cellulose sheet was cut into a desired shape by using a blanking blade, a laser cutter, and the like and the positive electrode 201 was thereby fabricated. Since the carbonized bacterial cellulose sheet had a sheet shape, processing into a desired shape was easy. Moreover, since the positive electrode 201 had the sheet shape, the flexibility of the sheet mask was not impaired and adhesion to the skin was improved.

Methods of fabricating the negative electrode, the separator, the electrically-conductive layer, the battery part, the sheet mask, and the active ingredient were the same as those of Example 1.

In the evaluation test, as in Example 1, the sheet mask 1 of Example 2 impregnated with the active ingredient was attached to a subject and, after 15 minutes, the moisture amount in the skin was measured. Results of the evaluation test are described later.

EXAMPLE 3

Example 3 was different from Example 2 in that the sheet mask main body 3 was made of an electrically-conductive substance to be used as the electrically-conductive layer 204 and multiple positive electrode portions 21 and negative electrode portions 22 were arranged on one electrically-conductive layer 204.

The positive electrode, the negative electrode, the separator, and the active ingredient were the same as those in Example 2.

The positive electrode portion 21 was fabricated by pressure-bonding the positive electrode 201 and the positive electrode portion separator 203A and the negative electrode portion 22 was fabricated by pressure-bonding the negative electrode 202 and the negative electrode portion separator 203B.

The sheet mask main body 3 used the same carbon cloth as the electrically-conductive layer 204 of Examples 1 and 2. The carbon cloth was cut out into a shape of a contour of the face and portions corresponding to the eyes and the mouth were cut out to fabricate the sheet mask main body 3.

As illustrated in FIG. 1, the multiple positive electrode portions 21 and the negative electrode portions 22 were arranged on the sheet mask main body 3.

In Example 3, the sheet mask main body 3 is shared by the multiple battery parts 2 as the electrically-conductive layer 204. Thus, there is no need to process the electrically-conductive layer 204 for each battery part 2 and the manufacturing cost can be reduced.

In the evaluation test, as in Example 1, the sheet mask 1 of Example 3 impregnated with the active ingredient was attached to a subject and, after 15 minutes, the moisture amount in the skin was measured. Results of the evaluation test are described later.

EXAMPLE 4

Example 4 was the same as Example 1 except for the material of the positive electrode 201.

The positive electrode 201 of Example 4 was fabricated by using carbon (Ketjenblack EC600JD) publicly-known to be used for an air electrode of a general magnesium-air battery. Specifically, Ketjenblack powder (manufactured by Lion Corporation) and polytetrafluoroethylene (PTFE) powder (manufactured by Daikin Industries, Ltd.) were sufficiently pulverized and mixed at a weight ratio of 50:30:20 by using a mortar machine and subjected to roll forming to be fabricated into a sheet-shaped electrode with thickness of 0.5 mm. The sheet-shaped electrode was cut into a desired shape by using a blanking blade and the positive electrode 201 was obtained.

Methods of fabricating the negative electrode, the separator, the electrically-conductive layer, the battery part, the sheet mask, and the active ingredient were the same as those of Example 1.

In the evaluation test, as in Example 1, the sheet mask 1 of Example 4 impregnated with the active ingredient was attached to a subject and, after 15 minutes, the moisture amount in the skin was measured. Results of the evaluation test are described later.

COMPARATIVE EXAMPLE 1

Figure 9:
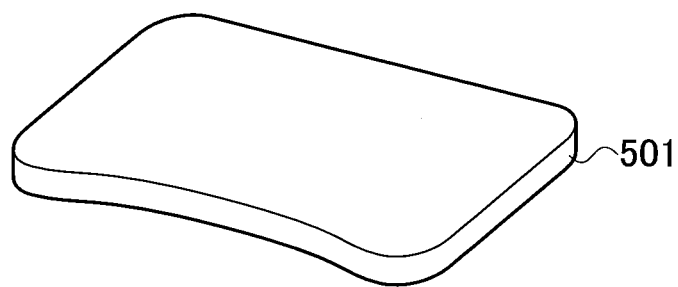
FIG. 9 is a perspective view of a separator portion in Comparative Example 1.
Figure 10:
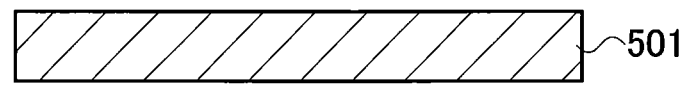
FIG. 10 is a cross-sectional view of the separator portion in Comparative Example 1.

FIG. 9 is a perspective view of a separator portion to be attached to a sheet mask main body of Comparative Example 1 and FIG. 10 is a cross-sectional view of the separator portion of Comparative Example 1.

A sheet mask using only the separator and the active ingredient which were the same as those in Example 1 was fabricated as a comparative example including no battery part.

The separator portion 501 was fabricated by cutting out a commercially-available cellulose cotton (BEMCOT, manufactured by Asahi Kasei Corporation) as in Example 1 into a desired shape by using a blanking blade, a laser cutter, and the like.

The separator portion 501 was arranged on the sheet mask main body 3 to correspond to the positive electrode portion 21 and the negative electrode portion 22 illustrated in FIG. 1.

The active ingredient to be impregnated into the sheet mask was prepared as described below as in Example 1. A carbonate aqueous solution with pH of 8.8 and an L-ascorbic acid (vitamin C) aqueous solution with concentration of 100 μmol/ml were mixed such that a mixture with pH of about 7.4 was prepared.

In the evaluation test, the sheet mask of Comparative Example 1 in which the separator portion 501 was impregnated with the active ingredient was attached to a subject and, after 15 minutes, the moisture amount in the skin was measured.

Table 1 illustrates the measurement results of Examples 1 to 4 and Comparative Example 1. Table 1 illustrates average values of moisture amounts in the skins of 100 subjects which were measured before usage, just after the usage, after one hour, after three hours, after five hours, and after 12 hours for Examples 1 to 4 and Comparative Example 1.

TABLE 1

|  | BEFORE USAGE | JUST AFTER USAGE | AFTER ONE HOUR | AFTER TWO HOURS | AFTER FIVE HOURS | AFTER 12 HOURS |
| --- | --- | --- | --- | --- | --- | --- |
| EXAMPLE 1 | 27% | 55% | 50% | 47% | 46% | 40% |
| EXAMPLE 2 | 27% | 56% | 51% | 48% | 47% | 43% |
| EXAMPLE 3 | 27% | 58% | 52% | 50% | 48% | 45% |
| EXAMPLE 4 | 27% | 48% | 43% | 39% | 38% | 34% |
| COMPARATIVE EXAMPLE 1 | 27% | 40% | 35% | 31% | 30% | 28% |

It is found that an increase in the skin moisture amount from that before the use of the sheet mask in each of Examples 1 to 4 is greater than that in Comparative Example 1. This is assumed to be because ionized L-ascorbic acid was introduced into the biological tissue simultaneously with the movement of the hydroxide ions into the biological tissue due to the battery reaction.

Meanwhile, in Comparative Example 1, an increase in the moisture amount was measured just after the use but the moisture amount decreased to about the same amount as that before the usage after 12 hours and no great change was observed.

It is found that the increase in the moisture amount in Example 2 is greater than that in Example 1. This is because the carbonized bacterial cellulose sheet was used for the positive electrode and adhesion between the skin and the sheet mask was improved.

It is found that the increase in the moisture amount in Example 3 is greater than that in Example 2. This is assumed to be because, in Example 3, the electrically-conductive layer was used while being shared by the battery parts and routes of ion currents flowing through the skin increased from those in the case where the electrically-conductive layer was provided for each battery, thereby promoting the effect of iontophoresis.

The increase in the moisture amount in Example 4 is smaller than those in Examples 1 to 3. Moreover, when the positive electrode of Example 4 was observed after the measurement, part of the positive electrode was destroyed and smear due to carbon powder was confirmed on the skin.

[Examples and Evaluation Results 2]

Next, description is given of Examples 5 to 8 using the battery part 2 of FIG. 6 and of evaluation results of these examples. Examples 5 to 8 each had a configuration in which the positive electrode portion electrically-conductive layer and the negative electrode portion electrically-conductive layer are brought into contact with the skin to make electrons flow to the skin. Examples 5 to 8 were examples in which the battery parts 2 of Examples 1 to 4 had the configuration of the battery part 2 of FIG. 6.

EXAMPLE 5

Example 5 was an example in which the battery part 2 of Example 1 had the configuration of the battery part 2 of FIG. 6.

Figure 11:
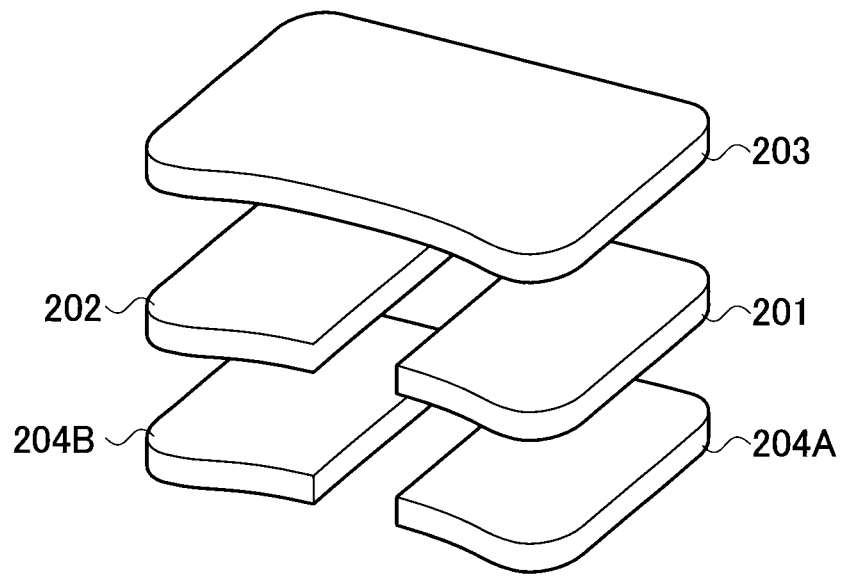
FIG. 11 is an exploded perspective view of a battery part in Example 4.
Figure 12:
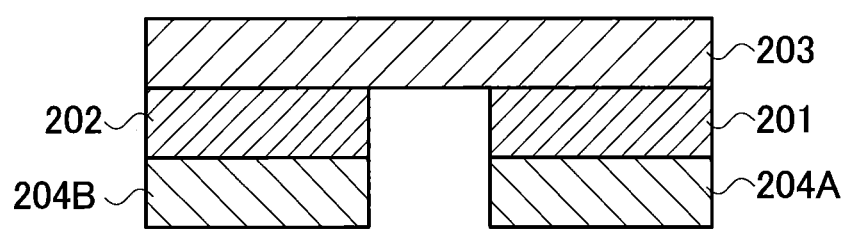
FIG. 12 is a cross-sectional view of the battery part in Example 4.

FIG. 11 is an exploded perspective view of the battery part 2 in Example 5. FIG. 12 is a cross-sectional view of the battery part 2 in Example 5.

The battery part 2 of Example 5 included the positive electrode 201, the negative electrode 202, the separator 203, the positive electrode portion electrically-conductive layer 204A, and the negative electrode portion electrically-conductive layer 204B. The battery part 2 of Example 5 was different from that of Example 1 in that the battery part 2 was configured to cause electrons to flow to the skin.

The elements of the battery part 2 were fabricated as in Example 1 and the battery part 2 of Example 5 was fabricated as follows. The positive electrode 201 and the negative electrode 202 were laid on the separator 203 and were sandwiched between the separator 203 and a set of the positive electrode portion electrically-conductive layer 204A and the negative electrode portion electrically-conductive layer 204B. Then, portions 1 mm inside outer peripheries of the positive electrode 201 and the negative electrode 202 were sewed by using a sewing machine to pressure-bond these elements and the battery part 2 was thus obtained.

As illustrated in FIG. 1, multiple battery parts 2 were arranged on the sheet mask main body 3.

The active ingredient impregnated into the sheet mask 1 was the same as that in Example 1.

In the evaluation test, as in Example 1, the sheet mask 1 of Example 5 impregnated with the active ingredient was attached to a subject and, after 15 minutes, the moisture amount in the skin was measured. Results of the evaluation test are described later.

EXAMPLE 6

Example 6 was an example in which the battery part 2 of Example 2 had the configuration of the battery part 2 of FIG. 6.

Example 6 was different from Example 5 in that a carbonized bacterial cellulose sheet containing carbonized bacterial cellulose and bacterial cellulose was used for the positive electrode.

A method of fabricating the positive electrode was the same as that in Example 2. Methods of fabricating the negative electrode, the electrically-conductive layer, the battery part, the sheet mask, and the active ingredient were the same as those in Example 5.

In the evaluation test, as in Example 1, the sheet mask 1 of Example 6 impregnated with the active ingredient was attached to a subject and, after 15 minutes, the moisture amount in the skin was measured. Results of the evaluation test are described later.

EXAMPLE 7

Example 7 was an example in which the battery part 2 of Example 3 had the configuration of the battery part 2 of FIG. 6.

Example 7 was different from Example 6 in that the sheet mask main body 3 was used as the separator 203 and the multiple positive electrode portions 21 and the negative electrode portions 22 were arranged on one separator 203.

The positive electrode, the negative electrode, the electrically-conductive layer, and the active ingredient were the same as those in Example 6.

The positive electrode portion 21 was fabricated by pressure-bonding the positive electrode 201 and the positive electrode portion electrically-conductive layer 204A and the negative electrode portion 22 was fabricated by pressure-bonding the negative electrode 202 and the negative electrode portion electrically-conductive layer 204B.

The sheet mask main body 3 used the same cellulose cotton as the separator 203 of Examples 5 and 6. The cellulose cotton was cut out into a shape of a contour of the face and portions corresponding to the eyes and the mouth were cut out to fabricate the sheet mask main body 3.

As illustrated in FIG. 1, the multiple positive electrode portions 21 and the negative electrode portions 22 were arranged on the sheet mask main body 3.

In Example 7, the sheet mask main body 3 is shared by the multiple battery parts 2 as the separator 203. Thus, there is no need to process the separator 203 for each battery part 2 and the manufacturing cost can be reduced.

In the evaluation test, as in Example 1, the sheet mask 1 of Example 7 impregnated with the active ingredient was attached to a subject and, after 15 minutes, the moisture amount in the skin was measured. Results of the evaluation test are described later.

EXAMPLE 8

Example 8 was an example in which the battery part 2 of Example 4 had the configuration of battery part 2 of FIG. 6.

Example 8 was the same as Example 5 ; except for the material of the positive electrode 201.

As in Example 4, the positive electrode 201 of Example 8 was fabricated by using carbon (Ketjenblack EC600JD) publicly-known to be used for an air electrode of a general magnesium-air battery.

Methods of fabricating the negative electrode, the separator, the electrically-conductive layer, the battery part, the sheet mask, and the active ingredient were the same as those in Example 5.

In the evaluation test, as in Example 1, the sheet mask 1 of Example 8 impregnated with the active ingredient was attached to a subject and, after 15 minutes, the moisture amount in the skin was measured.

Table 2 illustrates the measurement results of Examples 5 to 8. Table 2 also illustrates the measurement results of aforementioned Comparative Example 1. Table 2 illustrates average values of moisture amounts in the skins of 100 subjects which were measured before usage, just after the usage, after one hour, after three hours, after five hours, and after 12 hours for Examples 5 to 8 and Comparative Example 1.

TABLE 2

| | BEFORE USAGE | JUST AFTER USAGE | AFTER ONE HOUR | AFTER TWO HOURS | AFTER FIVE HOURS | AFTER 12 HOURS |
|---|---|---|---|---|---|---|
| EXAMPLE 5 | 27% | 55% | 51% | 46% | 46% | 39% |
| EXAMPLE 6 | 27% | 55% | 48% | 45% | 40% | 38% |
| EXAMPLE 7 | 27% | 56% | 50% | 49% | 45% | 41% |
| EXAMPLE 8 | 27% | 47% | 42% | 35% | 34% | 30% |
| COMPARATIVE EXAMPLE 1 | 27% | 40% | 35% | 31% | 30% | 28% |

It is found that an increase in the skin moisture amount from that before the use of the sheet mask in each of Examples 5 to 8 is greater than that in Comparative Example 1. Performances equivalent to those in Examples 1 to 4 in which ions are made to flow to the skin are obtained also in Examples 5 to 8 in which electrons are made to flow to the skin. It is found that excellent performances can be obtained in both of the case where electrons are made to flow to the skin and the case where the configuration of the battery part 2 is changed and ions are made to flow to the skin.

In Example 8, as in Example 4, part of the positive electrode was destroyed and smear due to carbon powder was confirmed on the skin.

As described above, according to the embodiment, the sheet mask 1 includes the multiple battery parts 2 arranged such that the electric currents flow along the mimic muscles or the flows of lymph. This allows the active ingredient to penetrate into the in-body tissues more effectively and also allows the mimic muscles and the lymphatic vessels to be electrically stimulated. Forming the battery part 2 by using materials with low environmental load allows easy disposal of the sheet mask 1 in everyday life.

According to the embodiment, the separator of each battery part 2 contains no electrolyte necessary for the battery reaction and, for use of the sheet mask 1, the battery reaction is started by impregnating the separator with the active ingredient. This can suppress self-discharging of the battery part 2 during storage of the sheet mask 1.

Note that the present invention is not limited to the embodiment described above and it is apparent that one having ordinary skill in the art can make many modifications and combinations within the technical scope of the present invention.

EXPLANATION OF THE REFERENCE NUMERALS 1 sheet mask
2 battery part
21 positive electrode portion
22 negative electrode portion
3 sheet mask main body
201 positive electrode
202 negative electrode
203 separator
203A positive electrode portion separator
203B negative electrode portion separator
204 electrically-conductive layer
204A positive electrode electrically-conductive layer
204B negative electrode electrically-conductive layer
100 biological tissue

The invention claimed is:

1. A sheet mask which is attached to a face for use, comprising:
a sheet mask main body; and
a battery part arranged on the sheet mask main body and configured to come into contact with the face when the sheet mask is worn, wherein the battery part includes a positive electrode portion, a negative electrode portion, and an electrically-conductive layer connecting the positive electrode portion and the negative electrode portion, wherein the positive electrode portion includes a positive electrode and a positive electrode portion separator, and the negative electrode portion includes a negative electrode and a negative electrode portion separator, wherein the positive electrode portion separator is arranged out of contact with the negative electrode and the negative electrode portion separator is arranged out of contact with the positive electrode, wherein the positive electrode portion separator is arranged out of contact with the negative electrode portion separator, and wherein the positive electrode portion separator and the negative electrode portion separator are configured to come into contact with the face when the sheet mask is worn.

2. The sheet mask according to claim 1, wherein for use of the sheet mask, the positive electrode portion separator and the negative electrode portion separator are impregnated with an active ingredient that serves a role of an electrolyte to start a battery reaction.

3. The sheet mask according to claim 1, wherein the sheet mask main body is configured to operate as the electrically-conductive layer of the battery part.

4. The sheet mask according to claim 1, wherein the positive electrode of the battery part contains carbonized cellulose having a three-dimensional network structure.

5. The sheet mask according to claim 1, wherein the negative electrode of the battery part contains at least one of magnesium, zinc, aluminum, iron, calcium, lithium, and sodium.

6. The sheet mask according to claim 1, wherein the battery part is arranged such that an electric current flows along a mimic muscle or a flow of lymph in the face.

7. A sheet mask which is configured to be attached to a face for use, comprising:
a sheet mask main body; and
a single battery part arranged on the sheet mask main body and configured to come into contact with the face when the sheet mask is worn, wherein the single battery part includes a positive electrode portion, a corresponding negative electrode portion, and a separator connecting the positive electrode portion and the negative electrode portion, wherein the positive electrode portion includes a positive electrode and a positive electrode portion electrically-conductive layer, the negative electrode portion includes a negative electrode and a negative electrode portion electrically-conductive layer, and wherein the positive electrode portion electrically-conductive layer is arranged out of contact with the negative electrode and the negative electrode portion electrically-conductive layer is arranged out of contact with the positive electrode, wherein the positive electrode portion electrically-conductive layer is arranged out of contact with the negative electrode portion electrically-conductive layer, and wherein the positive electrode portion electrically-conductive layer and the negative electrode portion electrically-conductive layer are configured to come into contact with the face when the sheet mask is worn.

8. The sheet mask according to claim 7, wherein the sheet mask main body is configured to operate as the separator of the single battery part.

\* \* \* \* \*